(12) United States Patent
Schudt

(10) Patent No.: US 6,333,354 B1
(45) Date of Patent: Dec. 25, 2001

(54) SYNERGISTIC COMBINATION OF PDE INHIBITORS AND ADENYLATE CYCLASE AGONISTS OR GUANYL CYCLYSE AGONISTS

(75) Inventor: Christian Schudt, Constance (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/367,850

(22) PCT Filed: Feb. 24, 1998

(86) PCT No.: PCT/EP98/01047
§ 371 Date: Aug. 27, 1999
§ 102(e) Date: Aug. 27, 1999

(87) PCT Pub. No.: WO98/37894
PCT Pub. Date: Sep. 3, 1998

(30) Foreign Application Priority Data

Feb. 28, 1997 (DE) ............................................. 197 08 049

(51) Int. Cl.[7] .......................... A61K 31/19; A61K 31/557; A61K 31/275
(52) U.S. Cl. .......................... 514/573; 514/520; 514/521; 514/523
(58) Field of Search .................................... 514/573, 520, 514/521, 523

(56) References Cited

U.S. PATENT DOCUMENTS

| 4,721,729 | * | 1/1988 | Skuballa et al. | 51/691 |
| 5,376,371 | * | 12/1994 | Bomabardelli | 424/195.1 |
| 6,013,827 | * | 11/2000 | Bordas-Nagy | 558/406 |

FOREIGN PATENT DOCUMENTS

| 96/06612 | | 3/1996 | (WO) . |
| WO-96/ 06612-A1 | * | 3/1996 | (WO) . |

OTHER PUBLICATIONS

Riva et al., "Iloprost Inhibits Neutrophil–Induced Lung injury and Neutrophil Adherence to Endothelial Monolayers" Am J Respir Cell Mol Biol, 3 (4). 1990. 301–310.*

Buerke et al.: "Synergistic platelet inhibitory effect of the phosphodiesterase inhibitor piroximone and iloprost:" Prostaglandins in the Cardiovascular System, 1992, 37/suppl. (71–77).*

O'Grady et al. "A chemically stable analot 9–beta methylcarbacyclin with similar effects to epoprostenol prostacyclin prostaglandin in I–2 in man" Br J Clin Pharmacol, 18(6). 1984 (921–934).*

Crutchley et al. "Effects of Prostacyclin Analogs on the Synthesis of Tissue Factor, Tumor Necrosis Facotr–alpha and Interleukin–1beta in Human Monocytic THP–1 Cells", J Pharmacol and Experimental Therapeutics, 271 (1). 1994. 446–451.*

Crutchley et al. "Prostacyclin Analogues Inhibit Tissue Factor Expression in the Human Monocytic Cell Line THP–1 Via a Cyclic AMP–Dependent Mechanism" Arterioscler. Thromb, 12(6), 1992. 664–670.*

Turner et al., Br. J. Pharmacol., "Pulmonary effects of type V cyclic GMP specific phosphodiesterase inhibition in the anaesthetized guinea–pig", (1994), 111, pp. 1198–1204.

Buerke et al., Prostaglandins in the Cardiovascular System, "Synergistic Platelet Inhibitory Effect of the Phosphodiesterase Inhibitor Piroximone and Iloprost", 1992 Birkhäuser Verlag Basel, pp. 71–77.

O'Grady et al.: "A Chemically Stable Analog 9–Beta Methylcarbacyclin With Similar Effects to Epoprostenol Prostacyclin Prostaglandin I–2 in Man", Br J Clin Pharmacol, 18 (6), 1984, 921–934.

* cited by examiner

Primary Examiner—Frederick Krass
Assistant Examiner—Donna Jagoe
(74) Attorney, Agent, or Firm—Jacobson Holman, PLLC

(57) ABSTRACT

A diseased state based on acute or chronic obstruction of vessels and/or bronchi, acute or chronic inflammation and/or edema formation is advantageously treated by the combined administration of a PDE inhibitor with either an adenylate cyclase agonist or a guanylate cyclase agonist to a subject in need of such therapy. Administration can be either concurrent or in either order.

6 Claims, No Drawings

SYNERGISTIC COMBINATION OF PDE INHIBITORS AND ADENYLATE CYCLASE AGONISTS OR GUANYL CYCLYSE AGONISTS

FIELD OF APPLICATION OF THE INVENTION

The invention relates to the combination of certain known active compounds for therapeutic purposes.

KNOWN TECHNICAL BACKGROUND

The substances used in the combination according to the invention are known active compounds from the class consisting of the PDE inhibitors and from the class consisting of the adenylate cyclase agonists and the guanylate cyclase agonists. Their combined use in the sense according to the invention for therapeutic purposes has not yet been described in the prior art.

DESCRIPTION OF THE INVENTION

The invention relates to the combined use of PDE inhibitors on the one hand and adenylate cyclase agonists or guanylate cyclase agonists on the other hand in the treatment of disease states which are based acute or chronic obstruction of vessels and/or bronchi, acute or chronic inflammation and/or edema formation.

PDE inhibitors within the meaning of the present invention are those compounds which slow the degradation of cyclic AMP (cAMP) and cyclic GMP (cGMP) by inhibition of the phosphodiesterases, which can lead to a relative increase in the intracellular concentration of cAMP and cGMP.

Possible PDE inhibitors within the meaning of the present invention are primarily those substances which are to be numbered among the class consisting of the PDE3 inhibitors, the class consisting of the PDE4 inhibitors and/or the class consisting of the PDE5 inhibitors, in particular those substances which can be designated as mixed types of PDE3/4 inhibitors or as mixed types of PDE3/4/5 inhibitors.

By way of example, those PDE inhibitors may be mentioned such as are described and/or claimed in the following patent applications and patents: DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EP0112987, EP0116948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5,141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DE1116676, DE2162096, EP0293063, EP0463756, EP0482208, EP0579496, EP0667345 and WO9307124.

Those PDE inhibitors are to be emphasized such as are claimed in the patent applications or patents EP0163965, EP0393500, EP0510562, EP0553174, WO9501338 and WO9603399.

PDE5 inhibitors which may be mentioned by way of example are RX-RA-69, SCH-51866, KT-734, vesnarinone, zaprinast, SKF-96231, ER-21355, BF/GP-385, NM-702 and sildenafil.

PDE4 inhibitors which may be mentioned by way of example are RO-20-1724, DENBUFYLLINE, ROLIPRAM, OXAGRELATE, NITRAQUAZONE, Y-590, DH-6471, SKF-94120, MOTAPIZONE, LIXAZINONE, INDOLIDAN, OLPRINONE, ATIZORAM, KS-506-G, DIPAMFYLLINE, BMY-43351, ATIZORAM, AROFYLLINE, FILAMINAST, PDB-093, UCB-29646, CDP-840, SKF-107806, PICLAMILAST, RS-17597, RS-25344-000, SB-207499, TIBENELAST, SB-210667, SB-211572, SB-211600, SB-212066, SB-212179 and GW-3600, CDP-840, in particular MOPIDAMOL, ANAGRELIDE, IBUDILAST, AMRINONE, PIMOBENDAN, CILOSTAZOL, QUAZINONE and N-(3, 5-dichloropyrid-4-yl)-3-cyclopropylmethoxy4-difluoromethoxybenzamide.

PDE3 inhibitors which may be mentioned by way of example are SULMAZOLE, AMPIZONE, CILOSTAMIDE, CARBAZERAN, PIROXIMONE, IMAZODAN, CI-930, SIGUAZODAN, ADIBENDAN, SATERINONE, SKF-95654, SDZ-MKS-492, 349-U-85, EMORADAN, EMD-53998, EMD-57033, NSP-306, NSP-307, REVIZINONE, NM-702, WIN-62582 and WIN-63291, in particular ENOXIMONE and MILRINONE.

PDE3/4 inhibitors which may be mentioned by way of example are BENAFENTRINE, TREQUINSIN, ORG-30029, ZARDAVERINE, L-686398, SDZ-ISQ-844, ORG-20241 and EMD-54622, in particular TOLAFENTRINE.

Adenylate cyclase agonists (AC agonists) within the meaning of the present invention are those compounds which accelerate the synthesis of cAMP via the enzyme adenylate cyclase, which leads to a relative increase in the intracellular concentration of cAMP.

AC agonists which may be mentioned in addition to the specific prostaglandins are, for example, adenosine, endothelium-specific growth factors (VEGF) and β-agonists, especially $β_2$-sympathomimetics. Among $β_2$-sympathomimetics, those selectively active substances may especially be mentioned which only have a slight cardiac action and are therefore also employed in the therapy of bronchial asthma. The following may be mentioned, for example, as appropriate $β_2$-sympathomimetics: salbutamol, tulobuterol, terbutalin, carbuterol, pirbuterol, isoxsuprine, reproterol, clenbuterol, fenoterol, bamethan, hexoprenaline, formoterol, salmeterol, picumeterol, rimiterol, procaterol, bambuterol, bitolterol, mabuterol, clorprenaline, isoetharine, etanterol, imoxiterol, naminterol, salmefamol and zinterol. In particular, those AC agonists may be mentioned such as are described and/or claimed in the patent applications EP0222413, EP0404652, DE2702553, DE2840142 and EP0011591. AC agonists which may be mentioned by way of example are KT-734, NKH-477, PACAP-38 and, in particular, iloprost and epoprostenol.

Guanylate cyclase agonists (GC agonists) within the meaning of the present invention are those compounds which accelerate the synthesis of cGMP via the enzyme guanylate cyclase, which leads to a relative increase in the intracellular concentration of cGMP.

GC agonists which may be mentioned in addition to the atrial natriuretic factor (ATF) or the atrial natriuretic peptide (ANP) are all substances forming nitrogen monoxide (NO) by biotransformation, in particular nitrates (such as, for example, glycerol trinitrate, isosorbide dinitrate, isosorbide mononitrate, pentaerythritol tetranitrate, sinitrodil) or sydnone imines (such as, for example, molsidomine).

Acceleration of the synthesis (by the AC agonists or by the GC agonists), like inhibition of degradation (by the PDE inhibitors) can lead to a relative increase in the intracellular concentration of cAMP and cGMP.

The biological effects of the combination following therefrom are not inevitably additive or even superadditive in cellular model systems. Surprisingly, on the isolated perfused lung of the rabbit a clearly superadditive synergistic effect was observed on the experimental pulmonary high blood pressure.

The unexpected, superadditive increase in the action of an AC agonist or of a GC agonist on the level and duration of the pulmonary blood pressure due to the simultaneous administration of a PDE inhibitor shows particular suitability for the treatment of disease states such as, for example, pulmonary hypertension. Moreover, a positive effect on the chronic changes in the vascular system or in the bronchial system ("remodeling") can be expected from a long-term treatment with such a combination. This applies to all disease states which are characterized by chronic angiopathy.

As a result of the combination according to the invention of PDE inhibitor and AC agonist or GC agonist, the individual components can be used in concentrations which are not very active or not active at all on their own. By this means, side effects of the individual components which would occur at the intrinsically active concentrations of PDE inhibitor or AC agonist or GC agonist on single administration are avoided by the low concentration in the combination.

Moreover, the effects of the combination are surprisingly also still markedly longer-lasting than the effects of the individual components.

Disease states which can be treated by the combination according to the invention and which may be mentioned by way of example are: pulmonary hypertension, chronic obstruction of vessels and airways (in the case of resistance or hypersensitivity to relaxing AC agonists—e.g. for bronchorelaxation—the action can be increased at relatively small concentrations by the additional administration of suitable PDE inhibitors), irreversible obstructions of vessels and bronchi (as a result of inflammatory diseases such as, for example, asthma, various cells are stimulated into growth by proliferation stimuli, which leads to the chronic constriction of the vessels and of the bronchi; the cell growth is slowed by the combination according to the invention and the obstructions known as "irreversible" in vessel and bronchi can be reduced), retinopathy, nephropathy, diabetic angiopathy, edema formation and inflammations (the transpulmonary lymphocyte kinetics and the granulocyte influx) can be effectively prevented.

One embodiment of the invention is the combined use of a PDE inhibitor selected from the group consisting of vesnarinone, zaprinast and sildenafil and of a guanylate cyclase agonist selected from the group consisting of ANP and NO (formed by biotransformation) for the treatment of the abovementioned disease states.

A preferred embodiment of the invention is the combined use of a PDE inhibitor selected from a group consisting of zardaverine and tolafentrine and of an adenylate cyclase agonist selected from the group consisting of iloprost and epoprostenol for the treatment of the abovementioned disease states.

"Combined use" within the meaning of the present invention is to be understood as meaning that the individual components can be administered simultaneously in a known and customary manner (in the form of a combination medicament), more or less at the same time (from separate pack units) or one after the other (directly one after the other or else also with a relatively large time interval).

With administration of the individual components more or less at the same time from separate pack units and with administration of the individual components taking place one after the other, it is possible, if desired, to select a different administration form. For example, one component can be administered by inhalation, while the other component is administered by infusion.

The dosage of the active compounds is carried out in an order of magnitude customary for the dosage of the individual components, it being possible on account of the individual actions, which are mutually positive and potentiating, for the respective dosages to be lowered on the combined administration of the active compounds compared with the standard. Dosages which may be mentioned by way of example for AC agonists are (in the case of administration to the patient by inhalation) 100–500 µg/kg of body weight for iloprost. For the PDE3/4 inhibitors zardaverine, for example, the otherwise customary dosage is 100–200 µg/kg of body weight, the synergistic action according to the invention being observed in animal experiments (isolated perfused and ventilated rabbit lung) even at doses of 1–20 µg/kg of body weight after conversion.

In the case of the PDE3/4 inhibitor tolafentrine, it was possible to observe a 50% fall in the (PGF2α-induced) pulmonary arterial pressure (PAP) in animal experimental batches in the isolated perfused and ventilated rabbit lung using 20 µmol/l. In the presence of aerosolized iloprost (170–510 µg/kg of rabbit lung), PAP is lowered by about 30% for 2–3 times the 15 min inhalation. On combined administration of iloprost and 0.1 µmol/l tolafentrine, PAP was lowered by >70%. This superadditive effect of the combination continues undiminished over the duration of the experiment of 3 h. A multiple increase in action and a marked prolongation of action are thus documented for the combined administration of iloprost and tolafentrine.

What is claimed is:

1. A method of therapeutic treatment of pulmonary hypertension which comprises administering an effective amount of medicament to a subject in need of such therapy, wherein the medicament comprises a combination of a) a PDE inhibitor with b) an adenylate cyclase agonist or a guanylate cyclase agonist, and wherein administration of a) and b) is either concurrent or in either order.

2. A method of therapeutic treatment of claim 1 wherein (a) is tolafentrine and (b) is iloprost or epoprostenol.

3. A method of therapeutic treatment of claim 2 wherein tolafentrine is administered in a dose which displays no thrapeutic action without a combination component.

4. A method of therapeutic treatment of claim 1 wherein (a) and (b) are substantially concurrently administered.

5. A method of therapeutic treatment of claim 2 wherein (b) is iloprost.

6. A method of therapeutic treatment of claim 2 wherein (b) is epoprostenol.

* * * * *